(12) United States Patent
Friess et al.

(10) Patent No.: US 6,197,341 B1
(45) Date of Patent: Mar. 6, 2001

(54) FORMULATIONS OF BALSALAZIDE AND ITS DERIVATIVES

(76) Inventors: Stefan Friess, Blankeneser Landstrasse 98, S-22587 Hamburg; Harald Heckenmüller, Wuelpensand 13, D-22559 Hamburg; Oliver Szambien, Pariner Strasse 1, D-23611 Bad Schwartau, all of (DE)

( * ) Notice: Subject to any disclaimer, the term of this patent is extended or adjusted under 35 U.S.C. 154(b) by 0 days.

(21) Appl. No.: 09/068,823

(22) Filed: May 14, 1998

Related U.S. Application Data

(63) Continuation of application No. PCT/SE98/00455, filed on Mar. 13, 1998.

(30) Foreign Application Priority Data

Mar. 14, 1997 (SE) .................................... 9700934-4

(51) Int. Cl.$^7$ ................. A61K 9/20; A61K 9/28
(52) U.S. Cl. .................... 424/474; 424/465; 424/464; 514/150; 514/960
(58) Field of Search .................... 424/464, 465, 424/490, 474, 480, 482; 514/150, 166

(56) References Cited

U.S. PATENT DOCUMENTS

| | | | |
|---|---|---|---|
| 3,915,951 | 10/1975 | Agback et al. | 260/156 |
| 4,045,429 | 8/1977 | Agback | 260/207 |
| 4,412,992 | 11/1983 | Chan | 424/226 |
| 5,316,772 | 5/1994 | Jurgens, Jr. et al. | 424/472 |
| 5,498,608 | 3/1996 | Johnson et al. | 514/150 |

FOREIGN PATENT DOCUMENTS

| | | | |
|---|---|---|---|
| 2 080 796 | 2/1982 | (GB) | C07C/107/06 |
| 81/02671 | 10/1981 | (WO) | A61K/31/60 |
| 92/06679 | 4/1992 | (WO) | A61K/9/16 |
| 95/18622 | 7/1995 | (WO) | A61K/31/615 |

*Primary Examiner*—James M. Spear
(74) *Attorney, Agent, or Firm*—Myers Bigel Sibley & Sajovec, P.A.

(57) ABSTRACT

The invention provides a unit formulation which comprises a 2-hydroxy-5-phenylazobenzoic acid derivative which is particularly sodium balsalazide dihydrate which formulation has a density of at least 0.9 mg/mm$^3$ and its use in the treatment of gastrointestinal diseases.

20 Claims, No Drawings

FORMULATIONS OF BALSALAZIDE AND ITS DERIVATIVES

This is a continuation of International Patent Application No. PCT/SE98/00455, with an international filing date of Mar. 13, 1998, now pending.

FIELD OF THE INVENTION

The present invention provides a new formulation of balsalazide.

BACKGROUND TO THE INVENTION

Balsalazide is a colon-specific, non-steroidal, anti-inflammatory aminosalicylate derivative which is useful in the treatment of gastrointestinal diseases, for example active ulcerative colitis and colon cancer (see WO 95/18622).

Balsalazide suffers from the disadvantage that a relatively high dose is required which makes it difficult to administer as a single dose. It is highly coloured and hence its administration as a solution is disadvantageous because it would stain the mouth. For compliance reasons the number of capsules to be swallowed by a patient per day should be as small as possible. When balsalazide is formulated as a capsule, the capsule has to be of such large dimensions that it is difficult, or impossible in some cases, to swallow whole.

A new formulation for balsalazide has now been found which solves or mitigates these problems.

SUMMARY OF THE INVENTION

According to the invention there is provided a unit formulation which comprises a compound of formula

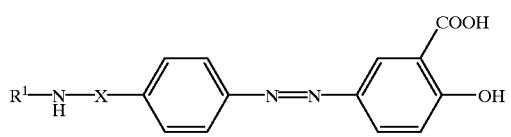

(I)

wherein
X represents $SO_2$ or CO;
$R^1$ represents phenyl, carboxymethylphenyl or $-R^2Y$;
$R^2$ represents $(CH_2)_n$ or benzyl-$(CH_2)_n$ wherein one or more of the hydrogen atoms of the alkylene moiety may be replaced by a $C_{1-6}$-alkyl, $NH_2$, $NH(C_{1-6}$-alkyl) or $N(C_{1-6}$-alkyl)$_2$ group;
Y represents COOH, $SO_3H$, OH, $NH_2$, $NHR^3$ or $N(R^3)_2$;
$R^3$ represents $C_{1-6}$-alkyl optionally substituted by a carboxylic or sulphonic acid group; and,
n is an integer from 1 to 6;
or an ester thereof; or an active metabolite thereof; or a non-toxic pharmaceutically acceptable salt thereof;
in association with one or more pharmaceutically acceptable excipients and/or binding agents;
which formulation has a density of at least 0.9 mg/mm$^3$.

The density of the formulation according to the invention is preferably at least 1.0 mg/mm$^3$, more preferably at least 1.1 mg/mm$^3$, most preferably at least 1.2 mg/mm$^3$ and preferably is at most 1.7 mg/mm$^3$, more preferably at most 1.4 mg/mm$^3$. The advantage of a formulation with a higher density is that the unit, e.g. tablet, size can be smaller, or, that for a set daily dose, the patient needs to take fewer tablets.

The compound of formula (I) is preferably sodium balsalazide dihydrate. The unit formulation is preferably solid, more preferably it is a tablet.

According to the invention there is further provided a method of manufacturing the unit formulation according to the invention which comprises granulating the compound of formula (I), optionally with a binding agent, compressing the granulate, optionally with other excipients and, optionally, coating the unit formulations obtained. The granulation step preferably only uses water and preferably this step is followed by the addition of a binding agent, for example crospovidone (preferably dry crospovidone).

The unit formulation according to the invention is substantially more dense than for example a capsule of 750 mg of sodium balsalazide dihydrate which is generally of size 00, i.e. it has a fill volume of 950 mm$^3$ (total volume of 1022 mm$^3$) and a density of 0.81 mg/ml without its shell and a density of 0.88 mg/ml with its shell.

The unit formulation according to the invention is preferably a tablet and preferably comprises the compound of formula (I) in granulated form, optionally granulated with a binding and/or disintegrating agent which is preferably in amount of less than about 10%, more preferably less than about 5% by weight relative to the total weight of the granulate. Suitable agents include water-soluble binding agents, crospovidone, croscarmellose sodium or maize starch. Examples of water-soluble binding agents include polyvinylpyrrolidone (especially in an amount of from 3% to 5% by weight), gelatin (especially in an amount of from 1% to 5% by weight), hydroxypropyl cellulose (especially in an amount of from 2% to 6% by weight), hydroxypropyl methylcellulose (especially in an amount of from 2% to 5% by weight), methylcellulose (especially in an amount of from 2% to 6% by weight), pregelatinised starch (especially in an amount of from 5% to 10% by weight).

The unit formulation according to the invention optionally further comprises one or more alternative excipients such as glidants, diluents and/or flavouring agents. Glidants such as for example silicon dioxide, stearylfumarate sodium, talc or magnesium stearate are preferably used in amounts of less than about 10% by weight, more preferably less than about 3% by weight relative to the total weight of the formulation. Diluents such as for example calcium phosphate are preferably used in amounts of less than about 30%, more preferably less than about 10% by weight relative to the total weight of the formulation. Flavouring agents such as for example menthol or sweeteners are preferably used in amounts of less than about 2%, more preferably less than about 0.5% by weight relative to the total weight of the formulation. The total amount of excipients in the unit formulation according to the invention is preferably from 0 to 70% by weight, more preferably from 1 to 30% by weight and most preferably from 1 to 10% by weight.

The unit formulation according to the invention is preferably provided with a coating, preferably a saliva resistant, optionally enteric, coating. The coating preferably comprises from 4 to 8% by weight of the unit formulation, more preferably about 6%. The coating is preferably a film coating comprising a polymer (for example hydroxypropylmethylcellulose, methyl cellulose, polymethylacrylate (for example Eudragit E, Eudragit L or Eudragit S) or ethylcellulose), a plasticiser (for example PEG, propylene glycol, glycerol and its esters or a phthalate ester) and/or a colourant, e.g. a water insoluble pigments.

There are various possible sizes for the unit formulation; these depend on the amount of active substance to be included in the formulation which depends upon the dosage regimen. For a preferred daily dose of 6.75 g of sodium balsalazide dihydrate, there are, for example, the following preferred dosage regimens:

(i) 3 units, each of about 750 mg of balsalazide, taken three times a day;
(ii) 2 units, each of about 1125 mg of balsalazide, taken three times a day; or
(iii) 1 unit of about 2250 mg of balsalazide, taken three times a day.

The invention further provides the unit formulation according to the invention for use in therapy, particularly for use in the treatment of gastrointestinal diseases, for example active ulcerative colitis and colon cancer. The invention also provides a method of treating a patient suffering from a gastrointestinal disease, which method comprises administering a therapeutically effective amount of a formulation according to the invention. The invention further provides the use of the formulation according to the invention in the manufacture of a medicament for use in the treatment of a gastrointestinal disease.

The invention is illustrated with reference to the following example which should not be interpreted as limiting the scope of the invention.

EXAMPLE 1

Tablets were prepared by mixing 6 parts by weight of sodium balsalazide and 0.32 parts by weight of crospovidone and wet granulating the mixture with about 1.12 parts by weight of purified water. The granulate was dried and then mixed in a dry blend mixer with 0.012 parts by weight of silicon dioxide and 0.032 parts by weight of magnesium stearate. The mixture was then compressed using a rotary press to yield uncoated tablets of 795.5 mg, having a density of 1.12 mg/mm³ and volume of 709 mm³. These were coated with a coating dispersion of 0.256 parts by weight of hydroxypropyl methyl cellulose (6 cps), 0.0768 parts by weight of talc and of polyethylene glycol 6000, and 0.0192 parts by weight of yellow coloured iron oxide and of reddish brown coloured iron oxide in about 2.816 parts by weight of purified water.

The coated tablets obtained had an average density of 1.19 mg/mm³ and a volume of 713 mm³ and were found to be at least 75% dissolved after 30 minutes in water (using the USP XXIII test method using test apparatus 2 (paddle), 100 rpm and 900 ml of distilled water at 37° C.).

What is claimed is:

1. A unit formulation which comprises a compound of formula

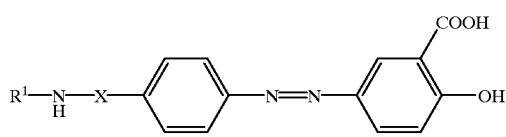

(I)

wherein
X represents $SO_2$ or CO;
$R^1$ represents phenyl, carboxymethylphenyl or —$R^2Y$;
$R^2$ represents $(CH_2)_n$ or benzyl-$(CH_2)_n$ wherein one or more of the hydrogen atoms of the alkylene moiety may be replaced by a $C_{1-6}$-alkyl, $NH_2$, $NH(C_{1-6}$-alkyl) or $N(C_{1-6}$-alkyl)$_2$ group;
Y represents COOH, $SO_3H$, OH, $NH_2$, $NHR^3$ or $N(R^3)_2$;
$R^3$ represents $C_{1-6}$-alkyl optionally substituted by a carboxylic or sulphonic acid group; and
n is an integer from 1 to 6;
or an ester thereof; or an active metabolite thereof; or a non-toxic pharmaceutically acceptable salt thereof;
in association with one or more pharmaceutically acceptable excipients or binding agents;
which formulation is in the form of a tablet having a density of at least 0.9 mg/mm³.

2. A formulation according to claim 1 wherein the compound of formula (I) is sodium balsalazide dihydrate.

3. A formulation according to claim 1 wherein the density of the formulation is from 1.1 to 1.7 mg/mm³.

4. A method of treating a patient suffering from a gastrointestinal disease, which method comprises administering to the patient a therapeutically effective amount of a formulation comprising:
a compound of formula I or a derivative thereof;

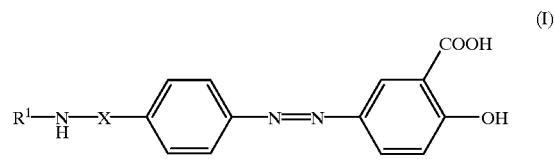

(I)

wherein
X represents $SO_2$ or CO;
$R^1$ represents phenyl, carboxymethylphenyl or —$R^2Y$;
$R^2$ represents $(CH_2)_n$ or benzyl-$(CH_2)_n$ wherein one or more of the hydrogen atoms of the alkylene moiety may be replaced by a $C_{1-6}$-alkyl, $NH_2$, $NH(C_{1-6}$-alkyl) or $N(C_{1-6}$-alkyl)$_2$ group;
Y represents COOH, $SO_3H$, OH, $NH_2$, $NHR^3$ or $N(R^3)_2$;
$R^3$ represents $C_{1-6}$-alkyl optionally substituted by a carboxylic or sulphonic acid group; and
n is an integer from 1 to 6;
and wherein the derivative is selected from the group consisting of esters, active metabolites, and non-toxic pharmaceutically acceptable salts;
in association with one or more pharmaceutically acceptable excipients or binding agents;
wherein the formulation is in the form of a tablet having a density of at least 0.9 mg/mm³.

5. The method according to claim 4, wherein the compound of formula I is sodium balsalazide dihydrate.

6. The method according to claim 4, wherein the density of the formulation is from 1.1 to 1.7 mg/mm³.

7. The method according to claim 4, wherein the gastrointestinal disease is active ulcerative colitis.

8. The method according to claim 4, wherein the gastrointestinal disease is colon cancer.

9. A method of manufacturing a tablet, said method comprising the steps of:
granulating a compound of formula I or a derivative thereof;

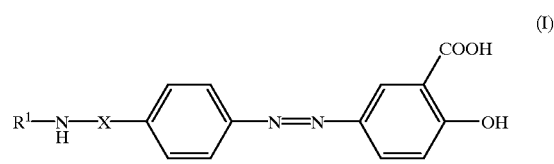

(I)

wherein
X represents $SO_2$ or CO;
$R^1$ represents phenyl, carboxymethylphenyl or —$R^2Y$;
$R^2$ represents $(CH_2)_n$ or benzyl-$(CH_2)_n$ wherein one or more of the hydrogen atoms of the alkylene moiety may be replaced by a $C_{1-6}$-alkyl, $NH_2$, $NH(C_{1-6}$-alkyl) or $N(C_{1-6}$-alkyl)$_2$ group;

Y represents COOH, $SO_3H$, OH, $NH_2$, $NHR^3$ or $N(R^3)_2$;

$R^3$ represents $C_{1-6}$-alkyl optionally substituted by a carboxylic or sulphonic acid group; and n is an integer from 1 to 6;

and wherein the derivative is selected from the group consisting of esters, active metabolites, and non-toxic pharmaceutically acceptable salts;

in association with one or more pharmaceutically acceptable excipients or binding agents;

and compressing the granulate to form a tablet having a density of at least 0.9 mg/mm$^3$.

10. The method according to claim 9, wherein the formulation is granulated with a binding agent in the granulating step.

11. The method according to claim 9, wherein the granulate is compressed with an excipient in the compressing step.

12. The method according to claim 9, further comprising the step of coating the tablet with a coating dispersion, wherein the compressing step precedes the step of coating.

13. A formulation according to claim 2, wherein the density of the formulation is from 1.1. to 1.7 mg/mm$^3$.

14. A method of manufacturing a tablet, said method comprising the steps of:

granulating sodium balsalazide dihydrate; and compressing the granulate to form a tablet having a density of at least 0.9 mg/mm$^3$.

15. The method according to claim 14, wherein the sodium balsalazide dihydrate is granulated with a binding agent in the granulating step.

16. The method according to claim 14, wherein the granulate is compressed with an excipient in the compressing step.

17. The method according to claim 14, further comprising the step of coating the tablet with a coating dispersion, wherein the compressing step precedes the step of coating.

18. The method according to claim 4, wherein the therapeutically effective amount is a dosage regimen of three tablets of the formulation, each tablet weighing about 750 mg, three times each day.

19. The method according to claim 4, wherein the therapeutically effective amount is a dosage regimen of two tablets of the formulation, each tablet weighing about 1125 mg, three times each day.

20. The method according to claim 4, wherein the therapeutically effective amount is a dosage regimen of one tablet of the formulation, each tablet weighing about 2250 mg, three times each day.

* * * * *